United States Patent
Marshall et al.

(10) Patent No.: US 7,616,793 B2
(45) Date of Patent: Nov. 10, 2009

(54) MEDICAL IMAGE REVIEW WORKSTATION WITH INTEGRATED CONTENT-BASED RESOURCE RETRIEVAL

(75) Inventors: Julian Marshall, Los Altos, CA (US); Keith W. Hartman, Redwood City, CA (US); Jimmy R. Roehrig, Aptos, CA (US)

(73) Assignee: Hologic, Inc., Marlborough, MA (US)

(*) Notice: Subject to any disclaimer, the term of this patent is extended or adjusted under 35 U.S.C. 154(b) by 639 days.

(21) Appl. No.: 11/026,603

(22) Filed: Dec. 30, 2004

(65) Prior Publication Data

US 2006/0147099 A1   Jul. 6, 2006

(51) Int. Cl.
G06K 9/00 (2006.01)
A61B 5/00 (2006.01)
G06F 19/00 (2006.01)
G06F 7/00 (2006.01)
G06F 17/30 (2006.01)

(52) U.S. Cl. .................... 382/128; 382/130; 705/3; 707/6

(58) Field of Classification Search ............... 382/128, 382/130; 705/3; 707/6
See application file for complete search history.

(56) References Cited

U.S. PATENT DOCUMENTS

| | | | |
|---|---|---|---|
| 4,945,476 A | | 7/1990 | Bodick et al. |
| 5,506,877 A | * | 4/1996 | Niklason et al. ............. 378/37 |
| 5,729,620 A | | 3/1998 | Wang |
| 5,815,591 A | * | 9/1998 | Roehrig et al. ............. 382/130 |
| 5,917,929 A | | 6/1999 | Marshall et al. |
| 5,974,201 A | | 10/1999 | Chang et al. |
| 6,482,156 B2 | | 11/2002 | Iliff |
| 6,630,937 B2 | | 10/2003 | Kallergi et al. |
| 2001/0043729 A1 | | 11/2001 | Giger et al. |
| 2003/0195883 A1 | * | 10/2003 | Mojsilovic et al. ............. 707/6 |
| 2004/0012601 A1 | * | 1/2004 | Sang et al. ................... 345/581 |
| 2004/0111299 A1 | * | 6/2004 | Onishi ............................ 705/3 |
| 2004/0122702 A1 | | 6/2004 | Sabol et al. |
| 2004/0122705 A1 | | 6/2004 | Sabol et al. |
| 2004/0122790 A1 | | 6/2004 | Walker et al. |
| 2006/0004761 A1 | * | 1/2006 | Maselli .......................... 707/9 |

OTHER PUBLICATIONS

Rodney et al. "Internet Access to Digital Medical X-Ray By Image Features and Associated Text", National Library of Medicine, Bethesda, MD 1998, pp. 900-904.*

(Continued)

*Primary Examiner*—John B Strege
(74) *Attorney, Agent, or Firm*—Brian J. Daiuto

(57) ABSTRACT

A review workstation for facilitating interpretation of a medical image by a user is described. The review workstation comprises a display device displaying the medical image to the user, and an input device receiving a graphical identification of a region of interest (ROI) in the medical image that is interesting to the user. Responsive to the identification of the ROI, a content-based image comparison is performed between the ROI and a resource database, the resource database comprising a collection of resource images previously analyzed by human interpreters and textual information associated with those previous analyses. The content-based image comparison comprises identifying a subset of the resource images similar to the ROI with respect to a preselected set of computed features. The display device subsequently displays to the user at least one of the identified subset of resource images and its associated textual information simultaneously with the ROI.

29 Claims, 5 Drawing Sheets

OTHER PUBLICATIONS

Naqa et al. "Content Based Image Retrieval For Digital Mammography", IEEE Proc, International Conference on Image Preocessing 2002, vol. 3, III-141/ III-144 (2002).*

Tang, et. al., "Histological Image Retrieval Based on Semantic Content Analysis," IEEE Transactions On Information Technology In Biomedicine, vol. 7, No. 1, 26-36 (Mar. 2003).

El Naqa, et. al., "Content-Based Image Retrieval For Digital Mammography", IEEE Proc. International Conference on Image Processing 2002, vol. 3, III-141-III-144 (2002).

Long, Rodney L., et. al., "Internet Access to Digital Medical X-Rays By Image Features and Associated Text," pp. 900-904, National Library of Medicine, Bethesda, MD (1998).

Orphanoudakis, Stelios C., et. al., "ICnet: Content-Based Similarity Search in Geographically Distributed Repositories of Medical Images," pp. 193-207, Computerized Imaging and Graphics, vol. 20, No. 4 (1996).

* cited by examiner

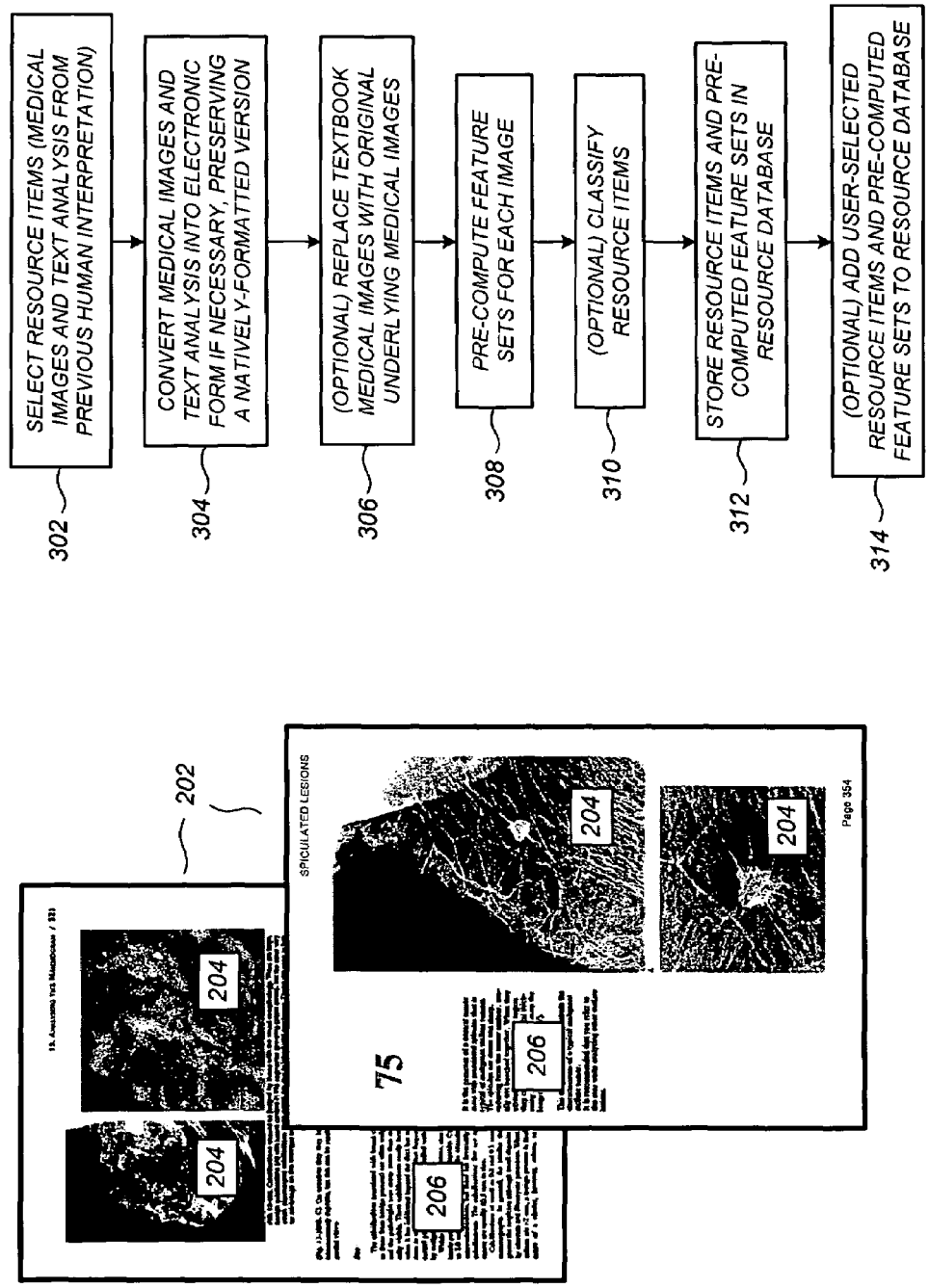

SIMILARITY RESULTS PAGE

FROM SELECTED TEACHING MATERIALS

[Jones89@236] Jones, M., *Female Mammography*, J. B. Lippincott Company (1989), Chapter 17 - Calcification Analysis, Section 17.2 - Cluster Shape, p. 236

[TabarDean85@98] Tabar, L and Dean, P., *Teaching Atlas of Mammography*, Georg Thieme Verlag (1985), Section B "Stellate Lesions, Heading "Key Case - 57," p. 91

...

FROM INTERNAL RESOURCES

[2003Kais_ABCD] Internal Mammography Case 2003_ABCD, Dr. William Smith, Client M. Doe, image set acquired 2003-05-05, CAD analysis date 2003-05-05, physician analysis date 2003-05-06....

[2004Kais_EFGH] Internal Mammography Case 2004_EFGH, Dr. M. Liu, Client W. Miller, image set acquired 2004-12-27, CAD analysis date 2004-12-27, physician analysis date 2004-12-30, ....

FROM WORLD WIDE WEB RESOURCES

[Creighton0023] Section 4: Evaluation of Calcifications.... Sample Reports: 1. Normal exam. .... Impression: New spiculated mass in left breast for which biopsy is recommended. .... Basic Radiology Imaging Lectures. radiology.creighton.edu/Mammography.html - 51k

[ACR007876] AMERICAN COLLEGE OF RADIOLOGY IMAGING NETWORK ACRIN 6667 to the MRI, and there must be no new breast symptoms.... 6 al, Radiology, 2003) the cancer yield women ... In a report by Kuhl et al, x-ray mammography revealed suspicious .... www.acrin.org/files/protocol_docs/A6667partial_summary.pdf

MEDICAL IMAGE REVIEW WORKSTATION WITH INTEGRATED CONTENT-BASED RESOURCE RETRIEVAL

FIELD

This patent specification relates to medical imaging. More particularly, this patent specification relates to systems and methods for facilitating human analysis of a medical image.

BACKGROUND

Computer-aided detection (CAD) generally refers to the use of computers to analyze medical images to detect anatomical abnormalities therein. Sometimes used interchangeably with the term computer-aided detection are the terms computer-aided diagnosis, computer-assisted diagnosis, or computer-assisted detection. The outputs of CAD systems are sets of information sufficient to communicate the locations of anatomical abnormalities, or lesions, in a medical image, and can also include other information such as the type of lesion, degree of suspiciousness, and the like. CAD results are most often communicated in the form of graphical annotations, generally referred to herein as CAD markers, overlaid upon a diagnostic-quality and/or reduced-resolution version of the medical image. CAD results are mainly used by radiologists as "secondary reads" or secondary diagnosis tools. As used herein, radiologist generically refers to a medical professional that analyzes medical images and makes clinical determinations therefrom, it being understood that such person might be titled differently, or might have differing qualifications, depending on the country or locality of their particular medical environment. When analyzing a medical image, the radiologist usually makes his or her own analytical determinations before looking at the CAD results, which either verify those determinations or trigger further inspection of the image. Some CAD implementations have used CAD results in a "concurrent reading" context in which the radiologists look at the CAD results at the same time that they look at the images.

In the field of x-ray mammography, thousands of mammography CAD systems are now installed worldwide, and are used to assist radiologists in the interpretation of millions of mammograms per year. Mammography CAD systems are described, for example, in U.S. Pat. No. 5,729,620, U.S. Pat. No. 5,815,591, U.S. Pat. No. 5,917,929, and U.S. 2001/0043729A1, each of which is incorporated by reference herein. Mammography CAD algorithms analyze digital or digitized images of standard mammographic views (e.g. CC, MLO) for characteristics commonly associated with breast cancer, such as calcifications, masses, and architectural distortions. It is to be appreciated that although presented in the particular context of x-ray mammography, the preferred embodiments described herein are applicable for a variety of medical imaging modalities such as computerized tomography (CT) imaging, magnetic resonance imaging (MRI), positron emission tomography (PET), single-photon emission computed tomography (SPECT), and ultrasound, and even less conventional medical imaging modalities such as thermography, electrical conductivity-based modalities, and the like.

In the context of medical image review workstations, including mammography CAD review workstations, key issues arise in the particular selection of information presented to the radiologist and the manner in which that information is presented. These issues are especially important in today's radiology environment, in which there is a ongoing tension between (i) providing high-quality detection/diagnosis for each patient, and (ii) maintaining adequate patient throughput to keep costs under control.

Substantial effort and attention has been directed to increasing the analysis capabilities of CAD systems and offering ever-increasing amounts of information for the radiologist to review at the workstation. By way of example, U.S. 2001/0043729A1, supra, discusses a search workstation in which the display shows both a computer classification output for a lesion as well as images of lesions from other medical images with known diagnoses based on a similarity of computer-extracted features. One or more shortcomings remain, however, in relation to the selection of relevant information that would be helpful to the radiologist in terms of quality and reliability of review. Further shortcomings remain relating to strategic integration of that helpful information into the existing radiology workflows.

Accordingly, it would be desirable to provide a medical review workstation that provides a judicious selection of helpful information to the radiologist for assisting in the screening and/or diagnosis of a medical image.

It would be further desirable to provide a user interface facilitating access to, and display of, that helpful information in an easily usable and time efficient manner.

SUMMARY

A system, method, and related computer program products are provided in the context of a review workstation for facilitating interpretation of a medical image by a user. The review workstation comprises a display device displaying the medical image to the user, and an input device receiving a graphical identification of a region of interest (ROI) in the medical image that is interesting to the user. Responsive to the identification of the ROI, a content-based image comparison is performed between the ROI and a resource database, the resource database comprising a collection of resource images previously analyzed by human interpreters and textual information associated with those previous analyses. The content-based image comparison comprises identifying a subset of the resource images similar to the ROI with respect to a preselected set of computed features. The display device subsequently displays to the user at least one of the identified subset of resource images and its associated textual information simultaneously with the ROI.

In one preferred embodiment, the resource database consists essentially of preselected, published medical reference texts and/or other medical teaching materials written by generally respected authors. The resource images and associated text therefrom are preferably displayed in their native published format. Displaying a resource item in its native published format next to the medical image under review provides for a degree of cognitive familiarity that can increase both the speed and quality of the review process.

Preferably, when multiple relevant resource items are found, an ordered list of selectable links is displayed, the user selecting one of the links to cause the simultaneous display of that resource item and the ROI. In one preferred embodiment, the resource database can additionally include unpublished resource images previously analyzed by human interpreters and associated textual information. Such resource items can be extracted, for example, from a non-public archive such as a hospital information system/radiology information system (HIS/RIS) database. Where multiple relevant resource items are found, the ordered listing is arranged and labeled such that the HIS/RIS resource items are clearly demarcated from the respected publication resource items. Optionally, the resource database can further comprise web-posted resource items, with the ordered listing further demarcating those results from the others.

In a mammography CAD environment, instantiation of the content-based image comparison is graphically achieved and seamlessly layered upon an existing mammography CAD user interface. To invoke the process, the user can select a displayed CAD marker, select a point location on the medical image near a center of the ROI, and/or graphically circumscribe the desired ROI. Notably, the ROI can generally comprise any location of interest to the user, regardless of whether it includes a CAD-marked location.

BRIEF DESCRIPTION OF THE DRAWINGS

FIG. 2 illustrates examples of medical reference text resource items in their native published format;

FIG. 3 illustrates populating a resource database according to a preferred embodiment;

FIG. 6 illustrates an ordered listing of content-based image comparison results segregated according to information resource type according to a preferred embodiment.

DETAILED DESCRIPTION

Figure 1:
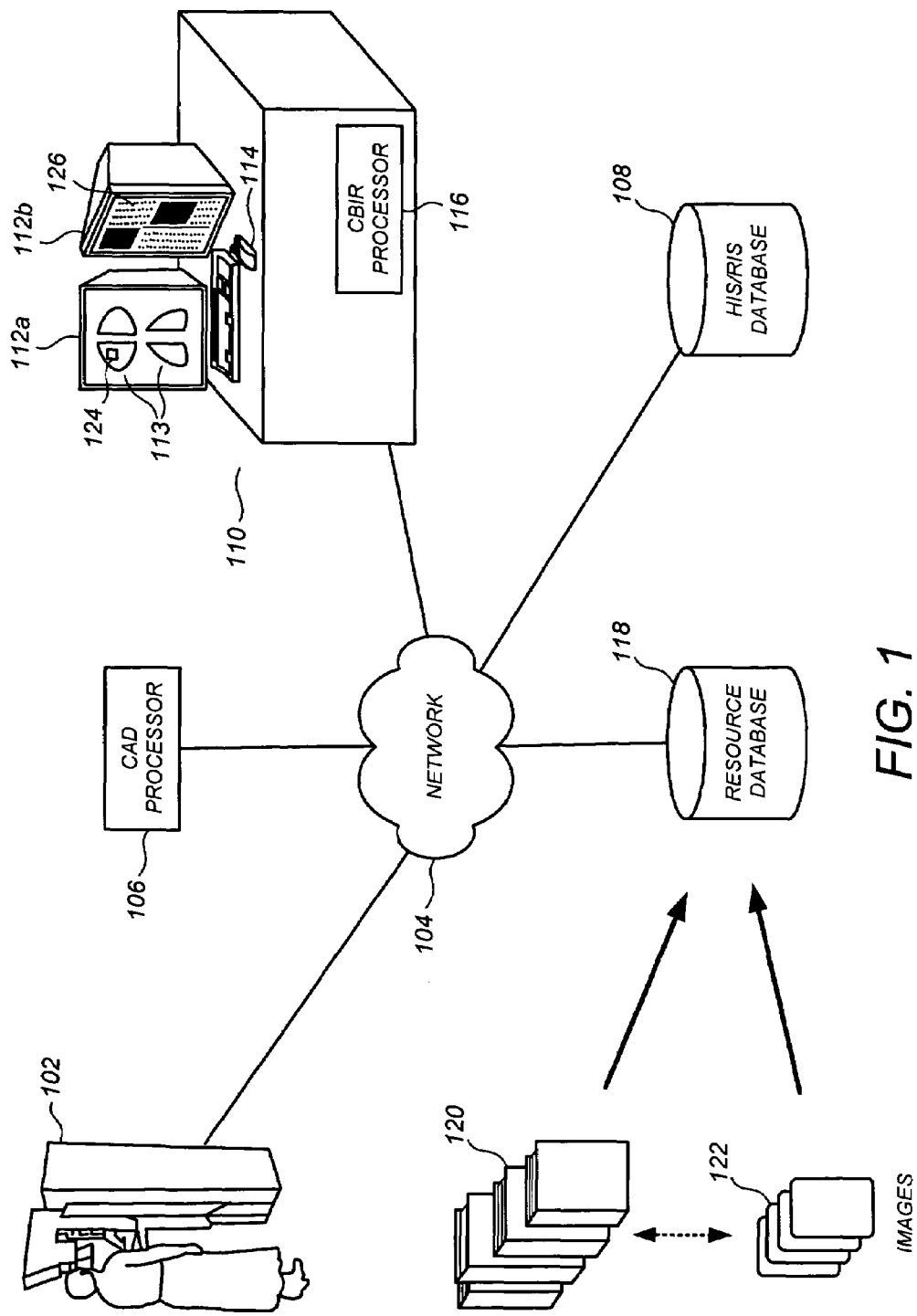
FIG. 1 illustrates a conceptual diagram of a mammography environment including a review workstation according to a preferred embodiment.

FIG. 1 illustrates a conceptual diagram of a mammography environment including a review workstation 110 according to a preferred embodiment. A mammogram acquisition device 102 acquires mammograms for patients, and can be either a film-screen system or a fully digital system. Although asymptomatic persons undergoing the mammographic imaging process are termed "clients" rather than "patients" in many clinics to denote that they are not symptomatic, the single term "patient" is used herein for simplicity and clarity of description. In the case of film-screen systems, a digitizer (not shown) is used to digitize the mammogram images before transfer to other electronic portions of the mammography environment.

Shown in FIG. 1 is a network 104, which may be a HIS/RIS (Hospital Information System/Radiology Information System) network, to which is coupled the mammogram acquisition device 102, a CAD processor 106, the review workstation 110, and a HIS/RIS database 108. The HIS/RIS database 108 generally represents a repository for medical information associated with the mammography environment, including both current and archived images, current and archived CAD results, radiology reports for completed cases, and so forth.

Notably, the mammography environment of FIG. 1 is presented by way of example only and is not intended to limit the scope of the preferred embodiments to this particular scenario. By way of example, different combinations of the devices of FIG. 1 can be placed adjacently to each other or integrated into the same hardware boxes without departing from the scope of the preferred embodiments. By way of still further example, the network 104 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments.

The preferred embodiments described herein are seamlessly layered upon an existing mammography CAD workflow, in which the digital or digitized mammogram images are processed by a CAD processor 106, and in which the mammogram images and their related CAD results are subsequently displayed on the review workstation 110 to a radiologist, who makes a clinical determination therefrom. The clinical determination can be in relation to screening, diagnosis, follow-up, or any of a variety of other activities.

According to a preferred embodiment, a resource database 118 is provided comprising a collection of resource images previously analyzed by human interpreters (e.g., radiologists) and textual information associated with those previous analyses. In one preferred embodiment, the resource database consists essentially of preselected, published medical reference texts and/or other medical teaching materials written by generally respected authors, termed herein respected publications. Although some degree of subjectivity is involved, most practitioners in the field of x-ray mammography, and other medical imaging fields, would be aware of a core set of experts and their associated publications that are commonly recognized as credible, authoritative references in the field. By way of mere example, most practitioners would agree that textbooks such as *Breast Imaging* by Dr. Daniel Kopans (Lippincott-Raven 1989) and *Teaching Atlas of Mammography* by Drs. Laszlo Tabar and Peter Dean (Georg Thieme Verlag 1985) would qualify as respected publications. Members of this class of respected publications, which are conceptually illustrated by texts 120 in FIG. 1, can be established by survey, selection by expert panel, or any of a variety of other methods. Often containing hundreds of medical images previously analyzed by the respected author, these reference items are particularly rich in content and are of particular usefulness to the reviewing radiologist. This usefulness is significantly enhanced when, according to a preferred embodiment, the relevant resource images are automatically identified based on similarity to the medical image under review, and then displayed simultaneously with the associated text next to the ROI. In other preferred embodiments, the published materials can include course handouts, journal articles, or more exotically-formatted materials such as tutorial CD's or PowerPoints, provided that they are selected and identified as respected publications by appropriately qualified radiologists.

FIG. 2 illustrates examples of medical reference text resource items 202 in their native published format, i.e., visually appearing in the layout, font, etc. as they were published. The resource items 202 include resource images 204 and associated textual information 206, as indicated in FIG. 2. Electronic versions of the resource items 202 are generated using known methods such as scanning paper documents, if necessary, and converting into PDF files or other appropriate electronic formats.

Notably, issues relating to copyright are beyond the scope of this disclosure, and for simplicity is it presumed herein that all necessary legal rights have been obtained. In one preferred embodiment, the original films or original digital images 122 for at least one of the respected publications is obtained from the author(s) or their successor-in-interest (i.e., persons legally possessing the images and the necessary rights). Although authors and publishers of respected publications are generally careful to maintain as much image quality as possible in the publication process, the published images are usually not as high-quality as the originals. Generation of computed image feature sets, the population of the resource database 118, and the quality of the content-based image comparison process are substantially improved by using the original films/images 122 according to this optional preferred embodiment.

Figure 4:
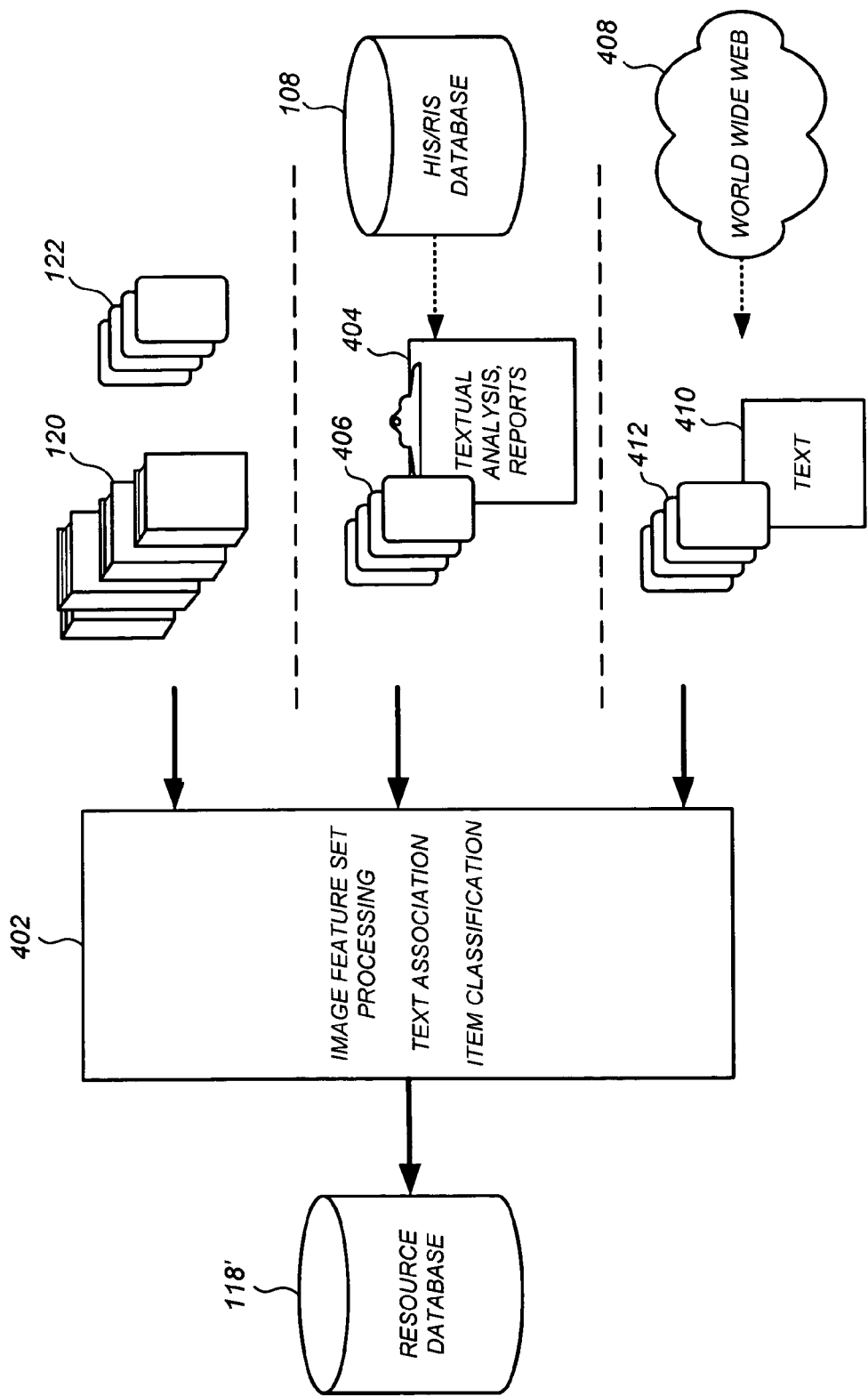
FIG. 4 illustrates a conceptual diagram of different types of resource items that can be included in a resource database according to a preferred embodiment.

FIG. 3 illustrates populating a resource database according to a preferred embodiment, which can be further understood with respect to FIG. 4. FIG. 4 illustrates a conceptual diagram of different types of resource items that can be included in a resource database 118' according to a preferred embodiment. At step 302, resource items (i.e., medical images and their associated textual information) are selected. In an alternative preferred embodiment as illustrated in FIG. 4, in addition to containing respected publications, the resource database can further comprise unpublished resource images 406 previously analyzed by human interpreters and associated textual information 404 as contained, for example, in a non-public archive such as the HIS/RIS database 108. Because medical image analysis is ultimately a human undertaking, reviewing these kinds of resource images together with their associated text 404, usually written by a colleague or predecessor at the same institution, can also be of high usefulness to the reviewing radiologist, especially when automatically accessed and displayed based on resource image similarity to the medical image under review.

In still another alternative preferred embodiment, the resource database 118' can further comprise web-posted resource items including web-posted resource images 412 and their associated textual information 410 obtained from the world wide web 408. Although likely to contain some highly credible and useful analyses, web-posted resource items are expected to statistically yield information less useful than the respected publications 120/122 or unpublished HIS/RIS cases 406/404, and are preferably segregated at least in terms of result listings on the user display.

At step 304, the reference items are converted into electronic form, if necessary, preferably while also preserving a natively formatted version. At step 306, the optional step of replacing published resource images with their underlying originals is performed, as discussed supra in relation to FIG. 2.

At step 308, the resource images are processed to compute one or more features according to a preselected feature set. Preferably, the preselected feature set includes most or all of the image features computed by the CAD algorithm performed by CAD processor 106 including, but not limited to size, spiculatedness, margin sharpness, eccentricity, sphericity, contrast, cluster characteristics, etc. The preselected feature set can also include additional image features such as overall breast density (i.e., percentage fat versus fibroglandular tissue) that might not be part of the CAD algorithm, but that can otherwise be a basis for visual similarity. Feature sets and methods similar to those discussed in U.S. 2001/0043729A1, supra, can also be used. Optionally, the preselected set of features may be altered on a per-case basis, a per-user basis, a per-institution basis, etc.

Depending on the particular make-up of the resource items selected at step 302, at step 310 the resource items are classified according to information resource type category, using categories such as "respected publication," "internal HIS/RIS", and "web-posted." Additional categories or other types of hierarchies relating to a generally expected degree of relevance and/or reliability can alternatively be used, e.g., "highly reliable", "moderately reliable," or "unverified", or the like, based on any of a variety of other objective or subjective criteria.

At step 312, the resource items and the precomputed feature sets are stored in the resource database 118/118'. One or more indexes for facilitating comparison of the medical images under review against the resource images based on computed feature sets can also be provided. Finally, at step 314, additional resource items can optionally be added to the resource database 118/118' on a per-user basis, per-institution basis, etc., as desired according to the professional opinions of qualified radiologists. The steps 308-314 are performed and/or facilitated by a processor 402, which may be separate from or integrated into the CAD processor 106 or other processing system.

Figure 5:
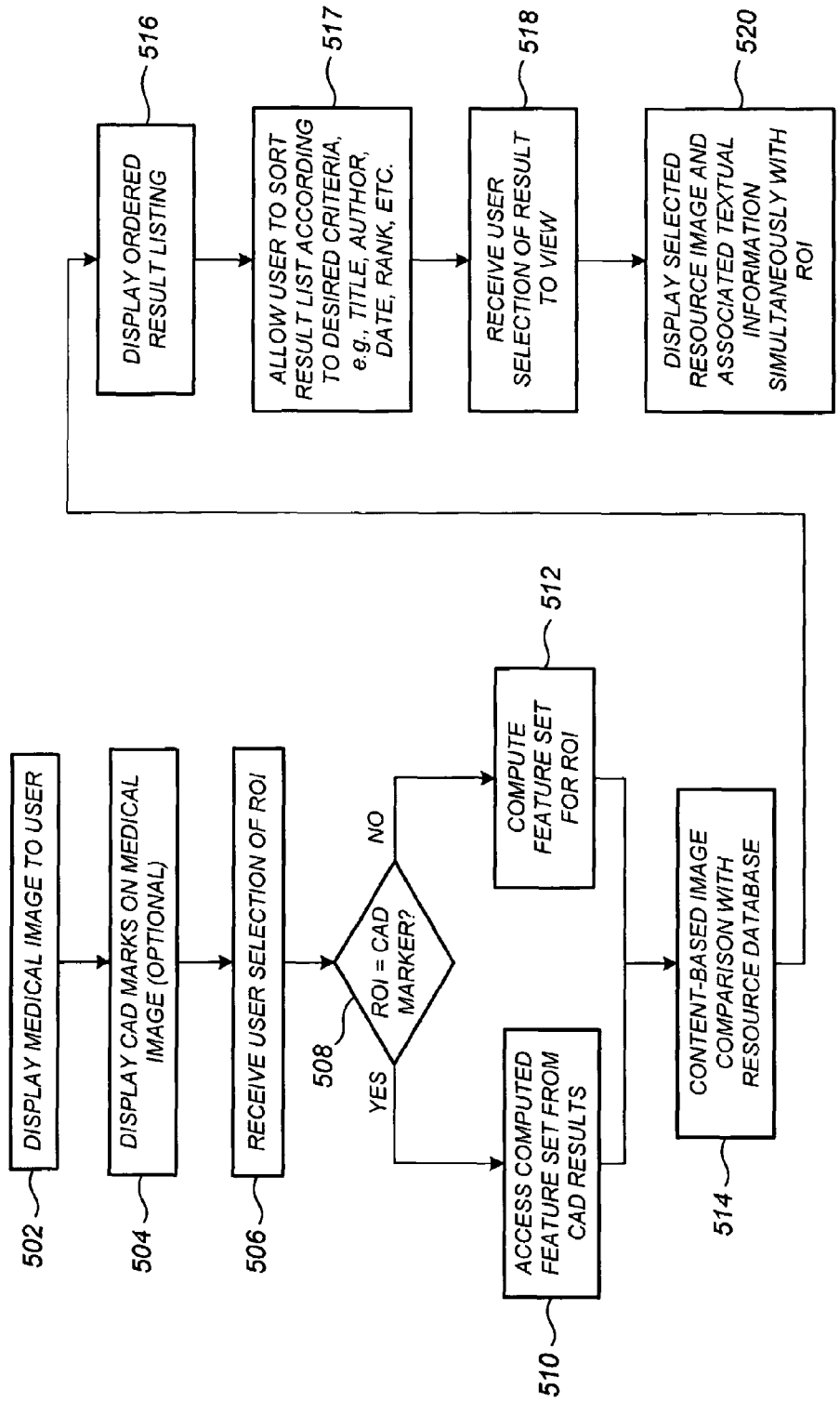
FIG. 5 illustrates facilitating review of a medical image according to a preferred embodiment.

FIG. 5 illustrates facilitating review of a medical image according to a preferred embodiment, and can be understood further with respect to FIG. 1, supra. At step 502, a medical image is displayed to the user, such as the mammogram 113 on a user display 112*a-b* of the review workstation 110 of FIG. 1. Notably, the user display 112*a-b* can be combined into a single larger monitor, separated onto three or more smaller monitors, etc. At step 504, CAD markers (not shown) can optionally be provided on the mammogram 113. At step 506, the user selects a region of interest (ROI) 124 that is interesting to the user which may, or may not, correspond to a CAD marker depending on the desire of the user. A mouse 114 is used to graphically identify the ROI 124, although any of a variety of graphical input devices can be used such as touch-screen monitors, pen-based pointers, and the like. To identify the ROI 124, the user can select a displayed CAD marker, select a point location on the medical image near a center of the ROI, and/or graphically circumscribe the desired ROI. Notably, the user can select the entire medical image as the ROI by circumscribing the entire medical image, or can just select a small portion thereof as in FIG. 1.

If the ROI 124 does not correspond to a CAD marker at step 508, a CBIR (content-based image retrieval) processor 116 computes an image feature set at step 512 associated with the ROI 124 that will serve as the basis for a content-based image comparison against the resource database 118/118'. The functionalities described herein for the CBIR processor 116 can optionally be performed by an accordingly-modified existing processor within the review workstation 110. If the ROI 124 does correspond to a CAD marker at step 408, then most of the image feature set required for the content-based image comparison will have already been computed by the CAD processor 106, so in one preferred embodiment the image feature set computed by the CAD processor 106 is stored in conjunction with the CAD results and, at step 410, is retrieved by the CBIR processor 116.

At step 514, content-based image comparison proceeds in accordance with methods such as those discussed in U.S. 2001/0043729A1, supra. If the CBIR processor 116 finds more than resource image meeting a predetermined and/or user adjustable similarity criterion with the ROI, an ordered listing containing user-selectable links is displayed to the user at step 516.

FIG. 6 illustrates a conceptual example of an ordered listing 602 displayed at step 516, for the optional case in which the resource database 118/118' contains more than one information resource type category. As illustrated, it is preferable to segregate the different information resource types for easy user recognition thereof. Each selectable link is accompanied by an identifier of the work that contains a resource image identified to be similar to the ROI, together with the section number, page number, heading, etc. associated therewith. The ordered listing 602 thus resembles and functions as a "bibliography" for the selected ROI. In one preferred embodiment, the similarity results page 602 is displayed on an ancillary monitor of the user display, which can be the monitor 112*b* of FIG. 1. In other preferred embodiments, the similarity results page 602 can be shown in a pop-up window next to the ROI 124, or in a dedicated frame of the user display. In one preferred embodiment, the ordered listing is user-sortable. At an optional step 517, the user is allowed to manipulate the ordered listing and sort the results by various criteria such as title, author, date, rank (i.e., relevance to medical image under review), etc. In another preferred embodiment, thumbnail images of the resource items can be displayed alongside the links.

Upon receipt of a selection by the user at step 518, at step 520 the selected resource image and associated textual information is displayed simultaneously with the ROI, as illustrated by resource item 126 in FIG. 1. In one preferred embodiment, the resource item 126 is displayed on the ancillary monitor 112b as shown in FIG. 1. In other preferred embodiments, it can be shown in a pop-up window or in a dedicated frame of the user display. Generally speaking, use of an ancillary monitor is preferred so as to achieve a more seamless layer of functionality upon an existing x-ray mammogram CAD workstation, although the scope of the preferred embodiments is not so limited. In one preferred embodiment, the resource item 126 is displayed in its native published format (see FIG. 2), the resource item 126 comprising the particular page of the located reference containing the similar resource image and its associated text.

In another preferred embodiment, semantic content-based image retrieval can be performed alternatively or in conjunction with computed feature-based image retrieval. Automatic generation of textual keywords descriptive of the selected ROI can be generated, in a manner analogous to one or more methods discussed in Tang, "Histological Image Retrieval Based on Semantic Content Analysis," IEEE Transactions On Information Technology In Biomedicine, Vol. 7, No. 1, 26-36 (March 2003). The textual information in the resource database is then text-searched based on the textual keywords, and identified resource items (resource images and text) are displayed to the user.

Notably, one of the above preferred embodiments in which the resource database 118 consists essentially of published materials 120 is advantageous with respect to regulatory issues such as FDA approval. Although the selection, retrieval, and presentation of the resource items is intelligently and conveniently achieved according to this preferred embodiment, the resource items themselves nevertheless represent published documents, and so little or no FDA approval issues are implicated.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although described in the context of a clinical radiology environment for facilitating quality and speed, the preferred embodiments supra can also advantageously be incorporated into a teaching environment in which the users are students. By way of further example, although the resource database 118 can contain full copies of all resource items used for a particular institution, the resource items can simply be links to externally stored complete copies of resource items that are network-accessible by the review workstation 110. By way of still further example, resource databases 118 can be merged across institutions, or the combined functionality of the resource database 118 and the CBIR processor 116 can be centralized at a single external application service provider, without departing from the scope of the preferred embodiments.

By way of still further example, it is to be appreciated that the term web-posted resource items can include any type of publicly available electronic resource item available over a network, regardless of whether the item appears at a "www" address or is transferred using the HTTP protocol. For example, web-posted resource items can include documents acquired from FTP-accessible databases, as well as documents acquired using Kazaa, BitTorrent, etc. (it being restated here that copyright issues are beyond the scope of the present disclosure and we simply presume here that appropriate legal rights have been obtained). In other preferred embodiments, the resource database is further populated with publicly available materials from shareware CD's, freeware CD's, and the like that are publicly available but not necessarily accessible over a network.

By way of still further example, according to another preferred embodiment a resource database update utility is provided to accommodate additional feature set characteristics selected subsequent to an initial feature pre-computation and indexing process. For example, if a new feature characteristic relevant to the CAD processing and/or the image similarity evaluation process is developed, the CBIR processor 116 and/or the processor 402 reprocesses the existing resource images to generate feature sets including that newly developed feature characteristic.

By way of even further example, in other preferred embodiments in which "real estate" on the user display is particularly limited (such as for laptop units or a budget "all-in-one" workstation), the resource items and the medical image under review can be displayed in a time-alternating fashion, e.g., using closable and moveable popup-windows, toggle buttons, or the like. Therefore, reference to the details of the preferred embodiments are not intended to limit their scope, which is limited only by the scope of the claims set forth below.

What is claimed is:

1. A workstation for facilitating interpretation of a medical image by a user, comprising:
 a display device displaying the medical image to the user;
 an input device receiving a graphical identification of a location of interest on the medical image from the user; and
 a processor performing a content-based image comparison of the location of interest against a resource database, said resource database comprising a collection of resource images previously analyzed by human interpreters and textual information associated with said previous analyses, said content-based image comparison comprising identifying a subset of said resource images similar to said location of interest with respect to a preselected set of computed features;
 wherein said resource database further comprises information categorizing each said resource image therein as being from one of:
  (i) a first category of medical data source consisting exclusively of preselected, published medical reference texts and medical teaching materials authored by an identified core set of expert authors and commonly recognized as credible and authoritative; and
  (ii) a second category of medical data source not qualified as being in said first category;
 and wherein said display device displays to the user at least one of said identified subset of resource images and its associated textual information simultaneously with said location of interest, said display device further displaying information identifying into which of said first and second categories the displayed resource image is categorized.

2. The workstation of claim 1, wherein at least one of the resource images from said first category of medical data source is replaced in said resource database by an original, high-quality digital or digitized image corresponding thereto acquired through the author or a successor-in-interest thereof.

3. The workstation of claim 1, said processor further performing the steps of:
automatically generating textual keywords descriptive of said location of interest based on said preselected set of computed features;
automatically text-searching said textual information associated with said previously analyzed resource images based on said textual keywords; and
displaying to the user at least one of said collection of resource images whose associated textual information is identified by said automatic text search.

4. The workstation of claim 1, wherein said medical image is a mammogram, and wherein said preselected set of computed features includes one or more of size, spiculatedness, margin sharpness, eccentricity, sphericity, average grey level, contrast, cluster characteristics, and breast density characteristics.

5. The workstation of claim 4, wherein said preselected set of features may be altered by the user.

6. The workstation of claim 1, wherein an ordered list of selectable links corresponding to said identified subset of resource images is displayed to the user, the user selecting one of said selectable links to cause said simultaneous display of the corresponding resource image and the location of interest.

7. The workstation of claim 6, wherein said second category of medical data source includes at least one of (i) unpublished resource images previously analyzed by human interpreters and associated textual information as contained in a non-public archive, and (ii) web-posted resource images previously analyzed by human interpreters and associated textual information.

8. The workstation of claim 1, wherein said displayed resource images that are from said first category of medical data source and their associated textual information are displayed in their native published format.

9. The workstation of claim 1, said display device displaying computer-aided detection (CAD) markers on said medical image, said graphical identification of a location of interest comprising user selection of one of said CAD markers.

10. The workstation of claim 1, said display device displaying computer-aided detection (CAD) markers on said medical image, said graphical identification of a location of interest comprising one or more of (a) user selection of one of said CAD markers, (b) user selection of a point location, wherein said location of interest comprises a predetermined pattern including said point location, and (c) user circumscription of a region corresponding to the location of interest, whereby either (b) or (c) may result in an identified location of interest that does not include any of said CAD markers.

11. A method for facilitating interpretation of a medical image, comprising:
identifying a first plurality of medical data sources meeting a predetermined selection criterion as being from published medical reference texts and medical teaching materials authored by an identified core set of expert authors and commonly recognized as credible and authoritative;
identifying a second plurality of medical data sources not meeting said predetermined selection criterion;
forming from said first and second pluralities of medical data sources a resource database comprising a collection of resource images previously analyzed by human interpreters and textual information associated therewith, wherein said resource database further comprises information categorizing each of the resource images into one of a first category and a second category according to the one of the first and second pluralities of medical data sources, respectively, with which its corresponding medical data source was identified;
displaying the medical image to a user;
receiving a graphical input from the user identifying a region of interest (ROI) in the medical image that is interesting to the user;
performing a content-based image comparison of the ROI against said resource database, said content-based image comparison comprising identifying a subset of said resource images similar to said ROI with respect to a predetermined computed image feature set; and
displaying to the user at least one of said identified subset of resource images and its associated textual information simultaneously with said ROI, and further displaying information identifying into which of the first and second categories the displayed resource image is categorized.

12. The method of claim 11, wherein at least one of the resource images categorized in said first category is replaced in said resource database by an original, high-quality digital or digitized image corresponding thereto acquired through the author or a successor-in-interest thereof.

13. The method of claim 11, further comprising:
automatically generating textual keywords descriptive of said ROI based on said predetermined computed image feature set;
automatically text-searching said textual information associated with said previously analyzed resource images based on said textual keywords; and
displaying to the user at least one of said collection of resource images whose associated textual information is identified by said automatic text search.

14. The method of claim 11, wherein said medical image is a mammogram, and wherein said predetermined computed image feature set includes one or more of size, spiculatedness, margin sharpness, eccentricity, sphericity, average grey level, contrast, cluster characteristics, and breast density characteristics.

15. The method of claim 14, wherein said predetermined computed image feature set may be augmented, reduced, and/or edited by the user.

16. The method of claim 11, further comprising:
displaying an ordered list of selectable links corresponding to said identified subset of resource images, wherein said ordered list includes information identifying into which of the first and second categories each listed resource image is categorized;
receiving a user selection of one of said selectable links; and
displaying the resource image corresponding to the selected link and the textual information associated therewith simultaneously with said ROI.

17. The method of claim 16, wherein said resource images categorized in said second category are acquired from at least one of (i) unpublished resource images previously analyzed by human interpreters and associated textual information as contained in a non-public archive, and (ii) web-posted resource images previously analyzed by human interpreters and associated textual information.

18. The method of claim 11, wherein said displayed resource images categorized in said first category and their associated textual information are displayed in their native published format.

19. The method of claim 11, further comprising displaying computer-aided detection (CAD) markers on said medical image, said CAD markers being generated by a CAD algorithm identifying anatomical abnormalities in the medical image based at least in part upon said predetermined computed image feature set, wherein said receiving the graphical input comprises receiving a user selection of one of said CAD markers.

20. The method of claim 11, further comprising displaying computer-aided detection (CAD) markers on said medical image, said CAD markers being generated by a CAD algorithm identifying anatomical abnormalities in the medical image based at least in part upon said predetermined computed image feature set, wherein said receiving the graphical input comprises one or more of (a) receiving a user selection of one of said CAD markers, (b) receiving a user selection of a point location, wherein said ROI comprises a predetermined pattern including said point location, and (c) receiving a user circumscription of the ROI, whereby either (b) or (c) may result in an identified ROI that does not include any of said CAD markers.

21. A CAD system for facilitating interpretation of a medical image, comprising:
a CAD processor for processing the medical image to detect anatomical abnormalities therein according to a CAD algorithm, the CAD algorithm computing a predetermined feature set for each potentially abnormal location within the medical image;
a display unit for displaying the medical image to a user and further displaying thereon CAD markers corresponding to detected anatomical abnormalities;
a graphical input unit for receiving a graphical identification of a region of interest (ROI) in the medical image that is interesting to the user;
a comparison processor for performing a content-based image comparison of the ROI against a resource database, said resource database comprising a collection of resource images previously analyzed by human interpreters and textual information associated therewith, said content-based image comparison comprising identifying a subset of said resource images similar to said ROI with respect to one or more features in said predetermined feature set, said display unit displaying to the user at least one of said identified subset of resource images and said associated textual information simultaneously with said ROI;
wherein said resource database further comprises information categorizing each said resource image therein as being from one of:
(i) a first category of medical data source consisting exclusively of preselected, published medical reference texts and medical teaching materials authored by an identified core set of expert authors and commonly recognized as credible and authoritative; and
(ii) a second category of medical data source not qualified as being in said first category;
and wherein said display unit further displays information identifying into which of said first and second categories the displayed resource image is categorized.

22. The CAD system of claim 21, wherein at least one of the resource images categorized in said first category is replaced in said resource database by an original, high-quality digital or digitized image corresponding thereto acquired through the author or a successor-in-interest thereof.

23. The CAD system of claim 21, wherein said medical image is a mammogram, and wherein said predetermined feature set includes one or more of size, spiculatedness, margin sharpness, eccentricity, sphericity, average grey level, contrast, cluster characteristics, and breast density characteristics.

24. The CAD system of claim 23, wherein said predetermined feature set of may be altered by the user.

25. The CAD system of claim 21, wherein graphical input unit receives one or more of (a) a user selection of one of said CAD markers, (b) a user selection of a point location, wherein said ROI comprises a predetermined pattern including said point location, and (c) a user circumscription of the ROI, whereby either (b) or (c) may result in an identified ROI that does not include any of said CAD markers.

26. The CAD system of claim 21, wherein said resource images categorized in said second category are acquired from at least one of (i) unpublished resource images previously analyzed by human interpreters and associated textual information as contained in a non-public archive, and (ii) web-posted resource images previously analyzed by human interpreters and associated textual information.

27. The CAD system of claim 26, wherein, prior to said simultaneous display, said display unit displays an ordered list of selectable links corresponding to said identified subset of resource images, said ordered list including information identifying into which of the first and second categories each listed resource image is categorized, said graphical input unit receiving a user selection of one of said selectable links.

28. The CAD system of claim 27, wherein said resource database is editable by the user and/or a user institution to add resource images/text, delete resource images/text, and/or recategorize a resource image and its associated text into a different category.

29. The CAD system of claim 21, wherein said displayed resource image and its associated textual information is displayed in its native published format if said displayed resource image is categorized in said first category.

* * * * *